(12) United States Patent
Pumarola Segura et al.

(10) Patent No.: US 9,226,517 B2
(45) Date of Patent: Jan. 5, 2016

(54) USE OF IMINOCYCLITOLS AS INHIBITORS OF BACTERIAL ADHERENCE TO EPITHELIAL CELLS

(75) Inventors: Sergio Pumarola Segura, Barcelona (ES); Josep Lluis Torres Simón, Barcelona (ES)

(73) Assignee: Taihua Shouyue (Hong Kong) International Co Limited, Hong Kong (CN)

( * ) Notice: Subject to any disclaimer, the term of this patent is extended or adjusted under 35 U.S.C. 154(b) by 0 days.

(21) Appl. No.: 13/636,155

(22) PCT Filed: Mar. 24, 2011

(86) PCT No.: PCT/EP2011/054561
§ 371 (c)(1),
(2), (4) Date: Sep. 20, 2012

(87) PCT Pub. No.: WO2011/117362
PCT Pub. Date: Sep. 29, 2011

(65) Prior Publication Data
US 2013/0011344 A1    Jan. 10, 2013

(30) Foreign Application Priority Data
Mar. 25, 2010 (EP) .................................... 10382068

(51) Int. Cl.
| | |
|---|---|
| *A61K 9/68* | (2006.01) |
| *A61K 31/445* | (2006.01) |
| *A23K 1/16* | (2006.01) |
| *A23C 9/13* | (2006.01) |
| *A23L 1/29* | (2006.01) |
| *A23L 1/30* | (2006.01) |
| *A61K 8/49* | (2006.01) |
| *A61K 31/4015* | (2006.01) |
| *A61K 31/45* | (2006.01) |
| *A61K 45/06* | (2006.01) |
| *A61Q 11/00* | (2006.01) |
| *G01N 1/38* | (2006.01) |

(52) U.S. Cl.
CPC ............ *A23K 1/1625* (2013.01); *A23C 9/1322* (2013.01); *A23L 1/296* (2013.01); *A23L 1/30* (2013.01); *A23L 1/3014* (2013.01); *A61K 8/4926* (2013.01); *A61K 31/4015* (2013.01); *A61K 31/45* (2013.01); *A61K 45/06* (2013.01); *A61Q 11/00* (2013.01); *G01N 1/38* (2013.01)

(58) Field of Classification Search
None
See application file for complete search history.

(56) References Cited

U.S. PATENT DOCUMENTS

| | | |
|---|---|---|
| 5,981,494 A | 11/1999 | Rademacher et al. |
| 2004/0176320 A1 | 9/2004 | Natunen et al. |
| 2009/0087501 A1 | 4/2009 | Cummins |
| 2011/0130352 A1 | 6/2011 | Liu et al. |
| 2011/0171328 A1 | 7/2011 | Zhou et al. |

FOREIGN PATENT DOCUMENTS

| | | | |
|---|---|---|---|
| CA | 2696874 A1 | 3/2008 | |
| CN | WO 2008/025249 A1 * | 3/2008 | ........... A61K 125/00 |
| EP | 0852948 A1 | 7/1998 | |
| JP | 5271085 A | 10/1993 | |
| JP | 2009/062306 A | 3/2009 | |
| WO | 03/002127 A1 | 1/2003 | |
| WO | 2009/152665 A1 | 12/2009 | |
| WO | 2010/029313 A1 | 3/2010 | |

OTHER PUBLICATIONS

Castillo et al.; Organic Letters; vol. 8, No. 26; pp. 6067-6070 (2006); article 4 pp.; Supporting Information 29 pp.*
Islam et al.; J. Antimicrobial Chemotherapy (2008); 62 (4), 751-757.*
International Search Report for PCT/EP2011/054561, ISA/EP, mailed May 19, 2011.

* cited by examiner

*Primary Examiner* — Jeffrey T Palenik
(74) *Attorney, Agent, or Firm* — Harness, Dickey & Pierce, PLC

(57) ABSTRACT

It comprises the use of D-fagomine or derivatives thereof in the prevention and/or coadjuvant treatment of bacterial infections, as well as to pharmaceutical, veterinary, or food and feed, pet food compositions containing them.

9 Claims, No Drawings

USE OF IMINOCYCLITOLS AS INHIBITORS OF BACTERIAL ADHERENCE TO EPITHELIAL CELLS

CROSS-REFERENCE TO RELATED APPLICATIONS

This application is a 371 U.S. National Stage of International Application No. PCT/EP2011/054561, filed Mar. 24, 2011. This application claims priority to European Patent Application No. 10382068.4, filed Mar. 25, 2010. The disclosures of the above applications are incorporated herein by reference.

The present invention relates to the use of iminocyclitols in the prevention and/or coadjuvant treatment of bacterial infections or microflora imbalances, as well as to pharmaceutical, veterinary, or food compositions containing them.

BACKGROUND ART

Bacterial adherence to mucosal surfaces is considered to be an important prerequisite for colonization and infection. A variety of molecules and macromolecular structures, collectively known as adhesins, binding entity coming from the bacterium, recognized and interact with receptors on the surface on the host cells.

Three principal types of adhesin-receptor interactions have been described. The first type of adhesive interaction is due to the binding of lectins with carbohydrate structures. The second type, of which a significant number of cases are known, involves recognition between a protein on the bacterium and a complementary protein on the mucosal surface. The third type, comprises the binding interactions that occur between hydrophobins, frequently involving hydrophobic moieties of proteins interacting with lipids.

The first type, the lectin adhesins are usually classified by sugar specifity. Specifity can be determined by inhibiting the adhesion with either simple or complex carbohydrates that compete with the binding of the adhesins to host cells.

Sharon et al. in the document "Bacterial adherence to cell surface sugars", *Ciba Found Symp*. 1981, vol.80, pp 119-41, describes that the attachment strains of *Escherichia coli* and *Salmonella* spp. to epithelial cells is inhibited by D-mannose. Unfortunately the active mannose concentration necessary to produce inhibition, is high, al least about 0.5 M. *Escherichia coli* is among the most common causes of diarrhea, to receptors on intestinal epithelial cells. *Escherichia coli* may colonize, too, the vaginal and periurethral area and ascend the urinary tract. Its adhesion to the epithelial cells is the initial step in the establishment of infection. Thus, the ability to attach to the mucosal surface is thought to be essential for *Escherichia coli* to colonize and to remain in the urinary tract.

The document, Jose A. Castillo et at "Fructose-6-phosphate aldolase in organic synthesis: preparation of D-Fagomine, N-alkylated derivatives, and preliminary biological assays" Organic Letter 2006, vol. 8, n°26, pp. 6067-6070, describes that D-fagomine and the N-alkylated derivatives $C_4$, $C_6$, $C_8$, $C_9$ and Ph-$CH_2$ do not show antimicrobial activity.

Other type of inhibitors are iminocyclitols also called iminosugars or azasugars. The document, Barira Islam et al. "Novel anti-adherence activity of mulberry leaves: Inhibition of *Streptococcus mutans* biofilm by 1-deoxynojirimycin isolated from *Morus alba*", *Journal of Antimicrobial Chemotherapy* 2008, vol. 62, pp. 751-757, describes the anti-microbial activity against *S. mutans* of 1-deoxynojirimycin, compound isolated from *M. alba*. DNJ is a glucosidase inhibitor. Unfortunately, these glucosidase inhibitors often cause intestinal discomfort and diarrhoea.

Other botanical extract are described in the following patent applications.

The patent application US20090087501 provides an oral composition having at least two botanical active ingredients derived from plants. The botanical active ingredients provide particularly efficacious antimicrobial, antioxidant, anti inflammatory, antiageing and/or healing properties to the oral composition.

The Japanese patent application JP19920073844 describes a toothpaste comprises an extract of Kuwahakubi and an extract of *Morus Alba*.

The Japanese patent application JP20070230719 describes an immunostimulant comprises water soluble extract of bark of mulberry, as an active ingredient.

The document Asano et al. "N-containing sugars from *Morus Alba* and their glycosidase inhibitory activities" Carbohydrate Research 1994, vol. 259. pp. 243-255, describes the N-containing sugars from the roots of *Morus Alba*, and the glycosidase inhibitory activities of these compounds.

Finally the patent application CA2696874 describes an effective fraction of alkaloids prepared from mulberry twig, and the pharmaceutical composition containing the effective fraction for preparing hypoglycemic agents.

Other documents describe sugars or imino sugars for different pharmaceutical applications. The patent application WO2009152665 describes a pharmaceutical composition comprises fagomine for treating and preventing diabetes. The patent application WO2010029313 describes alkaloids and imino sugars with activity against HCV (Hepatitis C virus) and RSV (respiratory syncytial virus). The patent application WO03002127 describes the use of a glycoinhibitor substance comprising a pyranose structure with at least one oligosaccharide for treatment an infectious disease.

Finally the patent application EP0852948 describes the use of inhibitors of glycosidase enzymes, such as α-galactosidase, in the treatment of malaria, endotoxic shock and septic shock. The inhibitors reduce the conversion of the toxin precursor to toxin, thereby reducing the amount of toxin circulating in malaria patients.

Thus, from what is known in the art, it is derived that the development of inhibitors of the bacterial adherences is still of great interest.

SUMMARY OF THE INVENTION

Inventors have found that the D-fagomine and its alkylated derivatives inhibit the bacterial adherence to epithelial cells which makes these compounds useful for the prevention and/ or coadjuvant treatment of infections caused by an enteric, oral or respiratory bacteria. They are advantageous since with concentrations of ppm contribute in preventing and/or treating bacterial infections, without producing side effects.

D-fagomine (2R, 3R, 4R)-2-hydroxymethylpiperidine-3, 4-diol, is a natural iminocyclitol, a polyhydroxylated piperidine which was first isolated from buckwheat seeds of *Fagopyrum esculentum moench* and later from *Castanospermum australe*, dry *Xhanthocercis zambesiaca* leave and *Morus bombycis* leaves. The D-fagomine (2R, 3R, 4R)-2-hydroxymethylpiperidine-3,4-diol is shows in the formula below.

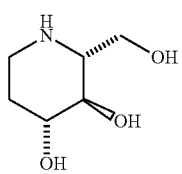

Nothing in the art suggests that the D-fagomine or its alkylated derivatives or its salts have the ability of inhibiting the adherence to epithelial cells of pathogen bacteria, and its practical value in the prevention and/or in the coadjuvant treatment of diseases where bacterial adherence is a prerequisite for the initiation of infection.

By inhibition of the adherence to epithelial cells of pathogen bacteria is meant to reduce contact between the receptors on the surface on the epithelial cells and the binding entity originated in the bacterium, the adhesins, specifically lectins, thereby preventing adhesion of the infectious agent. Since a better adherence enables bacterial survival; prevention of adhesion at an early stage, prevents the infection. There is compelling evidence showing that adherence to epithelial cells of enteric, oral and respiratory bacteria is required for colonization and that colonization is required for subsequent development of symtoms of diseases, Ofek et al., "Bacterial adhesion to animal cells and tissues", *ASM Press* 2003, chapter 1.

The inhibition not only prevent that the infection occurs but also is a useful coadjuvant for treating the infection. The adhesion mechanism is a process with multiple steps. It has been suggested that there are two distint kinetic steps, the first of which is readily reversible. Once the second step has taken place, the cell becomes firmly bound and the binding is only very slowly reversible. Therefore the first step of the adhesion mechanism can be reversible in the case that the adhesins of the bacteria has greater affinity for the antiadhesion agent and at a first step the bacterial infection can be treated.

Therefore, an aspect of the present invention relates to a compound of formula (I) or a pharmaceutically, veterinary or edible acceptable salt thereof, or alternatively, an enriched extract of natural origin comprising a compound of formula (I) or a pharmaceutically acceptable salt thereof, or a veterinary salt thereof or an appropriate edible salt thereof,

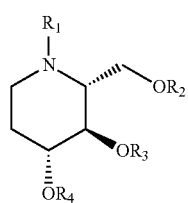

(I)

where $R_1$, $R_2$, $R_3$, $R_4$ is independently selected from the group consisting of H, $(C_1-C_{11})$-alkyl, and $CH_2Ph$, for use in the prevention and/or coadjuvant treatment of a bacterial infection or microflora imbalance caused by an enteric, oral or respiratory bacteria.

Another aspect of the present invention relates to a pharmaceutical composition comprising a compound of formula (I) or a pharmaceutically acceptable salt thereof, or alternatively, an enriched extract of natural origin comprising a compound of formula (I) or a pharmaceutically acceptable salt thereof as defined above, together with pharmaceutical excipients or carriers. Another aspect of the present invention relates to a veterinary composition comprising a compound of formula (I) or a veterinary acceptable salt thereof or alternatively, an enriched extract of natural origin comprising a compound of formula (I) or a veterinary acceptable salt thereof as defined above, together with veterinary excipients or carriers.

The compounds of the invention, particularly D-fagomine, help to improve gut flora by inhibiting the growth of harmful bacteria, for example *Escherichia coli*, but without inhibiting the beneficial bacteria, for example *Lactobacilli* and *Bifidobacteria*. This is because these compounds inhibit the bacterial adherence to epithelial cells in a selective form.

The presence of the compounds of the invention in the animal feed is associated with a decreased incidence of infectious diseases, and increased weight gain also called "growth promoting effect", this is because the compounds of the invention adhere to harmful bacterium, but not healthy bacteria, for example *Lactobacillus* or *Bifidobacterium* and other useful probiotics.

Therefore, it is possible to use D-fagomine and the alkylated derivatives as part of a nutritional composition food and feedstuff. This said functional food has a positive effect on the person's or animal's health by preventing bacterial infection caused by an enteric, oral or respiratory bacteria.

Therefore another aspect of the present invention relates to a food composition, pet food or feed composition comprising a compound of formula (I) or a appropriate edible salt thereof or alternatively, an enriched extract of natural origin comprising a compound of formula (I) or a edible acceptable salt thereof as defined above.

Most bacteria posses genes encoding more than one type of adhesin, a phenomenon that would require the use of multiple agents for multiple adhesins.

Thus, the compounds of the invention may be used alone or in combination with other suitable bioactive compounds or probiotics. In a particular embodiment, compounds of formula (I) or their salts can be used in prevention and/or coadjuvant treatment of a bacterial infection or microflora imbalance caused by an enteric, oral or respiratory bacteria, administered alone or in combination with a saccharide, iminocyclitol, probiotics or antibacterial agent.

Therefore, another aspect of the present invention relates to a combination of a compound of formula (I) or their salts or alternatively, an enriched extract of natural origin comprising a compound of formula (I) or a pharmaceutically acceptable salt thereof, or a veterinary salt thereof or an appropiate edible salt thereof as defined above, with a saccharide, a iminocyclitol, probiotic or an antibacterial agent, for the prevention and/or coadjuvant treatment of a bacterial infection or microflora imbalance caused by an enteric, oral or respiratory bacteria.

Another aspect of the present invention relates to a pharmaceutical composition, comprising a combination of a compound of formula (I) or a pharmaceutically acceptable salt thereof or alternatively, an enriched extract of natural origin comprising a compound of formula (I) or a pharmaceutically acceptable salt thereof as defined above, with a saccharide, a iminocyclitol, probiotic or an antibacterial agent, together with pharmaceutical excipients or carriers.

Another aspect of the present invention relates to a veterinary composition, comprising a compound of formula (I) or their veterinary acceptable salts or alternatively, an enriched extract of natural origin comprising a compound of formula (I) or a veterinary acceptable salt thereof as defined above, with a saccharide, a iminocyclitol, probiotic or an antibacterial agent, together with veterinary excipients or carriers.

Therefore another aspect of the present invention relates to a food, pet food or feed composition comprising a combination of a compound of formula (I) or their appropriate edible acceptable salts or alternatively, an enriched extract of natural origin comprising a compound of formula (I) or a edible acceptable salt thereof as defined above, with a saccharide, iminocyclitol or a probiotic.

It also forms part of the invention the compounds of formula (I) or their salts as defined above, for use as inhibiting agent of the adherence of enteric, oral or respiratory bacteria to epithelial cells.

DETAILED DESCRIPTION OF THE INVENTION

As mentioned above, an aspect of the present invention relates to compounds of formula (I) or their pharmaceutically, veterinary or appropriate edible acceptable salts, or alternatively, an enriched extract of natural origin comprising a compound of formula (I) or a pharmaceutically acceptable salt thereof, or a veterinary salt thereof or an appropiate edible salt thereof for use in the prevention and/or coadjuvant treatment of a bacterial infection or microflora imbalance caused by an enteric, oral or respiratory bacteria. In a preferably embodiment $R_1$, $R_2$, $R_3$, and $R_4$ are H.

This aspect of the invention can also be formulated as use of a compound of formula (I) or alternatively, an enriched extract of natural origin comprising a compound of formula (I) or their salts as defined above, for the preparation of a pharmaceutical or a veterinary composition, for the prevention and/or coadjuvant treatment of a bacterial infection or microflora imbalance caused by an enteric, oral or respiratory bacteria in a mammal, including a human. The invention also relates to a method of coadjuvant treatment and/or prophylasis of a mammal, including a human, suffering from or being susceptible to a bacterial infection or microflora imbalance caused by an enteric, oral or respiratory bacteria, said method comprising the administration to said mammal, including a human of an effective amount of the compounds of the present invention or alternatively, an enriched extract of natural origin comprising a compound of formula (I), including the known compounds mentioned above, together with acceptable excipients or carriers.

Non-limiting D-fagomine salts which may be used within the scope of the present invention are tartrate, hemitartrate, citrate, hemicitrate, chlorhidrate, malate, or acetate salts.

Because the D-fagomine occurs naturally in small amounts, preferably the plant extract is an enriched extract in order to be useful. Generally, the enriched plant extract comes from a plant selected from the group consisting of *Morus Alba*, and *Fagopyrun esculentum*. Preferably, the plant is *Fagopyrum esculentum*.

The term "enriched extract" as used herein, refers to an extract wherein the amount of active compound is higher than in the natural extract, obtained by physical or chemical methods.

The term "therapeutically effective amount" as used herein, refers to the amount of a compound that, when administered, is sufficient to prevent development of, alleviate to some extent, one or more of the symptons of the disorder, disease, microflora imbalance or condition being treated. The particular dose of compound administered according to this invention will of course be determined by the particular circumstances surrounding the case, including the compound administered, the route of administration, the particular condition being treated, and the similar considerations.

The term "saccharide" denotes saccharides epithelial cells receptor analog, for example methyl α mannoside, globotetraose, mannose, gal α(1 4) gal o linked methyl, sialyl 3' lactose, sialyl-gal (β1 4)GlcNAc, oxidized(α1 6) glucan.

The term "epithelial cells" denotes herein to any epithelial cells which cover the external surface of the body as well as the major body cavities.

The term "probiotic" denotes live microorganisms which, when administered in adequate amounts, confer a health benefit on the host, and it has not modified its adhesion to the intestinal mucosa with the presence of the iminocyclitols.

The term "$(C_1-C_{11})$-alkyl" denotes herein straight or branched chain alkyl. The D-fagomine for the purposes of the invention can be synthetic or of natural origin, in the form of a plant extract or purified substance.

The term "functional food" denotes herein any healthy food claimed to have a health-promoting or disease-preventing property beyond the basic function of supplying nutrients.

A particular embodiment is the compound of formula (I) or a pharmaceutically acceptable salt thereof, or a veterinary salt thereof or an appropiate edible salt thereof for use in the prevention and/or coadjuvant treatment of a bacterial infection or microflora imbalance caused by an enteric, oral or repiratory bacteria.

Preferably, the compounds of the invention are used in the prevention of a bacterial infection caused by an enteric, oral or respiratory bacteria.

In a particular embodiment the bacteria are selected from the group consisting of *Streptococcus mutans, Salmonella tphimurium, Escherichia coli, Streptococcus mitis, Streptococcus oralis, Streptococcus gordonii, Porphyromonas gingivalis, Aqgregatibacter actinomycetemcomitans, Fusobacterium nucleatum* and *Actinomices naeslundii*.

In a preferred embodiment, the compounds of the invention are used as coadjuvants in the treatment of a disease caused by the bacterial infection, which s selected from the group consisting of dental caries, periodontal disease, urinary disease, and intestinal disease.

In a preferred embodiment, the compounds of the invention are for use in the prevention and/or coadjuvant treatment of a bacterial infection or microflora imbalance caused by an enteric, oral or respiratory bacteria, by inhibiting the adherence of enteric, oral or respiratory bacteria to epithelial cells.

By the term "bacterial adherence" is understood the process whereby bacteria attach themselves to cells or other surfaces before proliferating.

As mentioned above a pharmaceutical composition or a veterinary composition comprising the compounds of the invention or alternatively, an enriched extract of natural origin comprising a compound of formula (I) or a pharmaceutically or veterinary acceptable salt thereof, together with pharmaceutical or veterinary excipients or carriers also form part of the invention.

In a preferred embodiment the pharmaceutical composition is a mouthwash, a gel, a liquid dental cleaning lotion, a tooth paste, a chewing gum, a denture cleaner or a prothesis adherence cream. In a more preferred embodiment, the pharmaceutical composition is a chewing gum.

Furthermore, it is possible to use the compounds of the invention as part of a nutritional composition food, pet food and feedstuff. The said functional food has a positive effect on the person's or animal's health by preventing bacterial infection and microflora imbalances caused by an enteric, oral or respiratory bacteria. Relevant areas of use in feed as a preventive of diseases in animal production are for example salmonellosis in chicken production, harmful microbism reduction in pig to obtain a better growth, or acidosis prevention in ruminants.

The compounds of the invention can also be used as a food or a beverage additive to produce a functional food or a functional beverage. Thus, they can be added to liquid food products or concentrates or powders, such as milk and liquid milk like products, various beverage including juices, soft drinks, sport drinks, alcoholic beverages, and the like. It is specially useful to have the compound of the invention as part of a food for an infant, preferably as a part of a infant formula. It is also relevant the interest of functional food including buckwheat with a remark on the content of D-fagomine, relevant examples could be beer, non-alcohol beer, tea like drink, milk like drink, pasta, biscuits, cookies, cereal bars, swollen grains, bread, crepes, cakes, creams, desserts, breakfast cereals and others that are enriched or standarized in its basic D-fagomine content. Yoghourt and derivatives are also relevant foods to be used together with selected probiotics.

The food or food additive can also be produced in a natural way, e.g. by having a domestic animal such a cow or other animal that produce D-fagomine in its milk. This can be accomplished by feeding the animal with *Fagopyrum esculentum*, *Morus alba* or purified D-fagomine Finally, as mentioned above the compounds of the invention may be used alone or in combination with other suitable bioactive compounds such as a saccharide, a iminocyclitol, probiotics or an antibacterial agent in prevention and/or coadjuvant treatment of a bacterial infection caused by an enteric, oral or respiratory bacteria. Pharmaceutical compositions, veterinary compositions food, pet food and feed products comprising the combination are also part of the invention.

The combinations of the invention may be used in the prevention and/or coadjuvant treatment of a bacterial infection caused by enteric, oral or respiratory bacteria. Preferably, the combinations are used in the prevention and/or coadjuvant treatment of a bacterial infection caused by an enteric, oral or respiratory bacteria by inhibiting the adherence of enteric, oral or respiratory bacteria to epithelial cells. Preferably the combination is for sequential, simultaneous or separate administration.

Non limiting probiotics which may be used within the scope of the present invention are: *Lactobacillus acidophilus*, *Lactobacillus rhamnosus*, *Lactobacillus bulgaricus*, *Lactobacillus salivarius*, *Lactobacillus plantarum*, *Lactobacillus casei*, *Lactobacillus sporogenes*, *Bifidobacteria bifidum*, *Bifidobacteria longum*, *Bifidobacteria infantis*

Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

The following examples are provided for illustrative means, and are not meant to be limiting of the present invention.

Example 1

Bacterial Agglutination Assay

Bacteria used in the assay were *Escherichia coli*, *Salmonella tphimurium* and *Streptococcus mutans*, from over night cultures. The bacteria were inoculated in the 100 ml flask with Luria medium. The bacteria were grown for 24 h at 37° C. After incubation, Agar Luria medium plates were inoculated. After 24 h suspensions of each strain were prepared in PBS medium ($10^8$ CFU/ml). Serial dilutions of the products to be tested, D-fagomine and D-fagomine tartrate (20 ppm, 200 ppm, 2000 ppm) were made. The dilutions were mixed with bacterial suspensions in a 1:1 ratio. After 90 min. at room temperature the suspensions were observed under optical microscope. They were compared with the control culture without any product added. It was found that the two products assay at 20 ppm, 200 ppm and 2000 ppm, agglutinated the cells of the three strains.

When the bacteria are agglutinated they lost their ability to adhere to other cells or substrate.

Example 2

Bacterial Agglutination Assay

Bacteria used in the assay were *Escherichia coli*, *Salmonella tphimurium*, *Streptococcus mutans*, *Lactobacillus casei* and *Bifidobacterium* sp., from over night cultures. The bacteria were inoculated in the 100 ml flask with Luria medium. The bacteria were grown for 24 h at 37° C. After incubation, Agar Luria medium plates were inoculated. After 24 h suspensions of each strain were prepared in PBS medium ($10^8$ CFU/ml). Serial dilutions of the product to be tested, D-fagomine tartrate (10 ppm, 20 ppm, 2000 ppm) were made. The dilutions were mixed with bacterial suspensions in a 1:1 ratio. After 90 min. at room temperature the suspensions were observed under optical microscope. They were compared with the control culture without any product added. The *Escherichia coli* and *Salmonella tphimurium* were compared with a positive control culture (mannose 0.05M).

It was found that the product assay, at 20 ppm and 200 ppm, agglutinated the cells of the three strains, *Escherichia coli*, *Salmonella tphimurium*, *Streptococcus mutans*, but not at 10 ppm. When the concentration of the product assay is 20 ppm, the agglutination was about 60% that of the corresponding positive control, and when the concentration is 200 ppm was about 70%. *Lactobacillus casei*, *Bifidobacterium* sp were not agglutinated by D-fagomine tartrate. When the bacteria are agglutinated they lost their ability to adhere to other cells or substrate.

Example 3

Anti-Adherence Activity of D-fagomine against *Streptococcus mutans*

Glass surface adherence assay was performed. The bacterium used in the assay was *Streptococcus mutans* from over night cultures ($1 \cdot 10^{10}$ UCF/ml). The bacterium was grown for 18 h at 37° C. in PBS medium. The bacteria from the overnight culture (0.25 ml) were grown for 18 h at 4° C. in a glass dish with the specific medium (0.5 ml). After the 18 h, 0.25 ml of D-fagomine (10 ppm, 20 ppm and 40 ppm) was added. In the control plate was added only PBS. After 90 min. the cells were transfered (0.5 ml) to a falcon tube, then were washed two times with PBS (0.5 ml each time). The wash of each bacteria was collected in a falcon tube and was kept at 4° C. The cells (100 µl) were seeded in the plates in TSA medium. The cells adhered were scrapped. In each well, it was added 0.5 ml of sterile PBS. The plaques with 100 µl were inoculated. The plaques were counted.

Results:

TABLE 1

Results of the recounted from glass and supernatant.
*Streptococcus* mutans

| concentration | Supernatant | glass | Total |
|---|---|---|---|
| 10 ppm | $4.15\ 10^4$ | $1.39\ 10^4$ | $5.54\ 10^4$ |
| 20 ppm | $4.12\ 10^4$ | $1.18\ 10^4$ | $5.30\ 10^4$ |
| 40 ppm | $5.17\ 10^4$ | $2.56\ 10^2$ | $5.20\ 10^4$ |
| Control, medium | $3.45\ 10^4$ | $2.10\ 10^4$ | $5.55\ 10^4$ |
| Control, mannose 0.05 M | $4.58\ 10^4$ | $8.70\ 10^3$ | $5.45\ 10^4$ |

TABLE 2

Results of the recounted from glass and supernatant.
*Streptococcus* mutans

| concentration | G/S | PG/CG | G/MG | G/Total |
|---|---|---|---|---|
| 10 ppm | $3.36\ 10^{-1}$ | 1.60 | 1.60 | $2.52\ 10^{-1}$ |
| 20 ppm | $2.86\ 10^{-1}$ | $5.61 10^{-1}$ | 1.35 | $2.22\ 10^{-1}$ |
| 40 ppm | $4.94\ 10^{-3}$ | $1.22\ 10^{-2}$ | $2.94\ 10^{-2}$ | $4.91\ 10^{-3}$ |
| Control, medium | $6.09\ 10^{-1}$ |  | 2.41 | $3.78\ 10^{-1}$ |
| Control, mannose 0.05 M | $1.90\ 10^{-1}$ | $4.14\ 10^{-1}$ |  | $1.60\ 10^{-1}$ |

G: glass S:supernatant
PG/CG: Product glass/Control glass(without product); colony forming units in glass by the action of D-fagomine or mannose 0.05 M/colony forming units in glass without product
G/MG: Glass/ Mannose glass; colony forming units in glass by the action of D-fagomine or medium/colony forming units in glass by the action of mannose 0.05 M
G/total: colony forming units in glass/total colony forming units inoculated.

It was found that D-fagomine, at 10 ppm, 20 ppm and 40 ppm, has antiadherence activity in respect of the control.

Example 4

Adhesion of *Salmonella* and *Escherichia coli* to Mucus in D-fagomine Presence

Mucus: mucosal epitelial cells
Adhesion to mucus. Protocol
Day 1
The bacteria was inoculated in the tube, with 3 ml Luria medium. The bacteria were grown for 24 h at 37° C. The tube was incubated overnight ($1\ 10^8$-$1\ 10^9$ UCF/ml).
Mucus Plate Preparation
The mucus (1 ml) is defrosted at room temperature. PBS medium (100 ml) was prepared. The defrosted mucus was centrifuged at 8000 rpm for 10 minutes. The mucus (1 ml) was transferred to an aliquot with sterile PBS (99 ml) (1:100). Each well is inoculated with 2.5 ml from the mixture and the plate is kept in the fridge (4° C.) overnight.
Day 2
Mucus Plate Wash
The plate was taken out from the fridge. 2 ml was extracted from each well. PBS (1 ml) was added, then was extracted, at the end there was 0.5 ml in the well.
Assay
The tubes that were grown overnight were diluted ($1\ 10^7$ UCF/ml).
The final volume in each well was: PBS 0.5 ml plus bacterial suspension 0.5 ml plus D-fagomine 0.5 ml (or PBS in control case).
Two plates were prepared (duplicated strains). Product concentration in the wells (10 ppm, 20 ppm, 40 pppm). Mannose concentration 0.05M (control well).

The wells were inoculated and the plates were incubated at 37° C. for 90 minutes.
After the 90 minutes, the supernatant of each well (10 µl) were observed under optical microscope.
It was added 1 ml of each well in eppendorfs. The eppendords were kept on the fridge. Two wash were made with PBS. The wells washed of the same strain were recoleted in a falcon tube and they were kept at 4° C. PBS (1 ml) was added in each well and the plates were inoculated with 100 µl of each tubes at the adecuated dilutions.
Day 3
The plates were recounted

TABLE 3

Supernatant recounted with D-fagomine 10 ppm, 20 ppm, 40 ppm

|  | Supernatant (UCF/ml) | Mucus UCF/ml | Supernatant/ mucus UCF/ml | Total UCF/ml | Bacteria in supernatant (%) |
|---|---|---|---|---|---|
| 10 ppm |  |  |  |  |  |
| *Salmonella* mutans 1 | $3.35\ 10^8$ | $3.00\ 10^7$ | $1.12\ 10^1$ | $3.65\ 10^8$ | 91.8 |
| *Salmonella* mutans 2 | $1.64\ 10^8$ | $4.50\ 10^7$ | 3.63 | $2.90\ 10^8$ | 78.4 |
| *Escherichia coli* 1 | $9.88\ 10^7$ | $2.50\ 10^7$ | 3.95 | $1.24\ 10^8$ | 94.5 |
| *Escherichia coli* 2 | $1.75\ 10^8$ | $9.00\ 10^6$ | $1.95\ 10^1$ | $1.84\ 10^8$ | 95.1 |
| 20 ppm |  |  |  |  |  |
| *Salmonella* mutans 1 | $1.10\ 10^8$ | $2.00\ 10^6$ | $5.51\ 10^1$ | $1.12\ 10^8$ | 98.2 |
| *Salmonella* mutans 2 | $2.84\ 10^8$ | $1.34\ 10^7$ | $2.11\ 10^1$ | $2.97\ 10^8$ | 95.5 |
| *Escherichia coli* 1 | $1.05\ 10^8$ | $4.00\ 10^6$ | $2.63\ 10^1$ | $1.09\ 10^8$ | 96.3 |
| *Escherichia coli* 2 | $1.00\ 10^8$ | $9.95\ 10^5$ | $1.01\ 10^2$ | $1.01\ 10^8$ | 99.0 |
| 40 ppm |  |  |  |  |  |
| *Salmonella* mutans 1 | $3.80\ 10^8$ | $7.00\ 10^6$ | $5.43\ 10^1$ | $3.87\ 10^8$ | 98.2 |
| *Salmonella* mutans 2 | $7.35\ 10^7$ | $1.39\ 10^7$ | 5.27 | $8.74\ 10^7$ | 84.1 |
| *Escherichia coli* 1 | $1.20\ 10^8$ | $1.00\ 10^6$ | $1.20\ 10^2$ | $1.21\ 10^8$ | 99.2 |
| *Escherichia coli* 2 | $7.00\ 10^7$ | $9.95\ 10^5$ | $7.04\ 10^1$ | $7.10\ 10^7$ | 98.6 |

TABLE 4

Supernatant recounted with Mannose

|  | Supernatant (UCF/ml) | Mucus UCF/ml | Supernatant/ mucus UCF/ml | Total UCF/ml | Bacteria in supernatant (%) |
|---|---|---|---|---|---|
| Manose 0.05% |  |  |  |  |  |
| *Salmonella* mutans 1 | $3.95\ 10^8$ | $1.00\ 10^6$ | $3.59\ 10^2$ | $3.96\ 10^8$ | 99.7 |
| *Salmonella* mutans 2 | $3.74\ 10^8$ | $1.50\ 10^7$ | $2.49\ 10^1$ | $3.89\ 10^8$ | 96.1 |
| *Escherichia coli* 1 | $2.98\ 10^8$ | $2.50\ 10^6$ | $1.19\ 10^2$ | $3.01\ 10^8$ | 99.2 |
| *Escherichia coli* 2 | $2.96\ 10^8$ | $2.45\ 10^6$ | $1.21\ 10^2$ | $2.98\ 10^8$ | 99.2 |

TABLE 5

Supernatant recounted with culture medium

|  | Supernatant (UCF/ml) | Mucus UCF/ml | Supernatant/ mucus UCF/ml | Total UCF/ml | Bacteria in supernatant (%) |
|---|---|---|---|---|---|
| Culture medium |  |  |  |  |  |
| *Salmonella* mutans 1 | $1.20\ 10^6$ | $3.96\ 10^6$ | $3.03\ 10^{-3}$ | $3.97\ 10^8$ | 0.30 |
| *Salmonella* mutans 2 | $1.40\ 10^6$ | $3.85\ 10^7$ | $3.64\ 10^{-3}$ | $3.99\ 10^8$ | 0.35 |

TABLE 5-continued

Supernatant recounted with culture medium

| | Supernatant (UCF/ml) | Mucus UCF/ml | Supernatant/ mucus UCF/ml | Total UCF/ml | Bacteria in supernatant (%) |
|---|---|---|---|---|---|
| Escherichia coli 1 | $1.50\ 10^6$ | $3.90\ 10^6$ | $3.85\ 10^{-3}$ | $3.91\ 10^8$ | 0.38 |
| Escherichia coli 2 | $1.45\ 10^6$ | $3.97\ 10^6$ | $3.66\ 10^{-3}$ | $3.98\ 10^8$ | 0.36 |

The microorganisms are significantly in the supernatant, not in the mucus. In the presence of D-fagomine the microorganisms are aglutinated between them and they are not agglutinated with the mucus, independently of the D-fagomine concentration.

Example 5

Adhesion of Lactobacillus and Bifidobacterium to Mucus in D-fagomine Presence Adhesion to mucus. Protocol Day 1

The bacteria was inoculated in the tube with 3 ml Luria medium. The bacteria were grown for 24 h at 37° C. The tube was incubated overnight ($1\ 10^7$-$1\ 10^8$ UCF/ml).

Mucus Plate Preparation

The mucus (1 ml) is defrosted at room temperature. 100 ml of PBS medium was prepared. The defrosted mucus (1 ml) was centrifuged at 8000 rpm for 10 minutes. The mucus (1 ml) was transferred to an aliquot with sterile PBS (99 ml). Each well is inoculated with 2.5 ml from the mixture and the plate is kept in the fridge (4° C.) overnight.

Day 2

Mucus Plate Wash

The plate was taken out from the fridge an the wash was made. 2 ml was extracted from each well. PBS (1 ml) was added, then was extracted, at the end there was 0.5 ml in the well.

Assay

The tubes that were grown overnight, were diluted ($1\ 10^7$ UCF/ml).

The final volume in each well was: PBS 0.5 ml plus bacterial suspension 0.5 ml plus D-fagomine 0.5 ml (or PBS in control case). It was prepared 2 plates (duplicated strains). Product concentration in the wells (10 ppm, 20 ppm, 40 pppm). Mannose concentration 0.05M (control well). The wells were inoculated and the plates were incubated at 37° C. for 90 minutes. After the 90 minutes, the supernatant of each well (10 µl) were observed under optical microscope. It was added 1 ml of each well in eppendorfs. The eppendords were kept on the fridge. Two wash were made with PBS. The wells washes of the same strain were recoleted in a falcon tube and they were kept at 4° C. PBS (1 ml) was added in each well and the plates were inoculated with 100 µl of each tubes at the adecuated dilutions.

Day 3

The plates were recounted

Results

TABLE 6

Supernatant recounted with D-fagomine 10 ppm, 20 ppm, 40 ppm, cultive medium and manose.*Lactobacillus acidophilus*

| Concentration | Supernatant | Mucus | Total |
|---|---|---|---|
| 10 ppm | $2.68\ 10^6$ | $2.23\ 10^6$ | $4.91\ 10^6$ |
| 20 ppm | $2.87\ 10^6$ | $2.23\ 10^6$ | $5.10\ 10^6$ |
| 40 ppm | $3.35\ 10^6$ | $1.58\ 10^6$ | $4.93\ 10^6$ |
| Cultive medium (Control) | $4.50\ 10^6$ | $4.00\ 10^5$ | $4.90\ 10^6$ |
| Manose 0.05 M (Control) | $3.30\ 10^6$ | $1.70\ 10^6$ | $5.00\ 10^6$ |

TABLE 7

Supernatant recounted with D-fagomine 10 ppm, 20 ppm, 40 ppm, cultive medium and manose. *Bifidobacterium*

| Concentration | Supernatant | Mucus | Total |
|---|---|---|---|
| 10 ppm | $1.20\ 10^7$ | $6.86\ 10^4$ | $1.21\ 10^7$ |
| 20 ppm | $1.20\ 10^7$ | $7.99\ 10^4$ | $1.21\ 10^7$ |
| 40 ppm | $1.20\ 10^7$ | $2.45\ 10^5$ | $1.22\ 10^7$ |
| Cultive medium (Control) | $1.20\ 10^7$ | $7.00\ 10^4$ | $1.21\ 10^7$ |
| Mannose 0.05 M (Control) | $1.07\ 10^7$ | $3.05\ 10^5$ | $1.10\ 10^7$ |

TABLE 8

Supernatant recounted with D-fagomine 10 ppm, 20 ppm, 40 ppm, cultive medium and manose. *Lactobacillus acidophilus*

| | M/S | Product M/ Control M | M/Manose M | M/Total |
|---|---|---|---|---|
| 10 ppm | $8.33\ 10^{-1}$ | 5.58 | 1.31 | $4.55\ 10^{-1}$ |
| 20 ppm | $7.78\ 10^{-1}$ | 5.58 | 1.31 | $4.38\ 10^{-1}$ |
| 40 ppm | $4.70\ 10^{-1}$ | 3.94 | $9.27\ 10^{-1}$ | $3.20\ 10^{-1}$ |
| Cultive medium (Control) | $8.89\ 10^{-2}$ | | $2.35\ 10^{-1}$ | $8.16\ 10^{-2}$ |
| Manose 0.05 M (Control) | $5.15\ 10^{-1}$ | 4.25 | 1.31 | $3.40\ 10^{-1}$ |

M: Mucus, S: supernatant, Product, D fagomine or Mannose

TABLE 9

Supernatant recounted with D-fagomine 10 ppm, 20 ppm, 40 ppm, cultive medium and manose. *Bifidobacterium*

| | M/S | Product M/ Control M | M/ Manose M | M/Total |
|---|---|---|---|---|
| 10 ppm | $5.71\ 10^{-3}$ | $9.80\ 10^{-1}$ | $2.25\ 10^{-1}$ | $5.68\ 10^{-3}$ |
| 20 ppm | $6.67\ 10^{-3}$ | 1.14 | $2.62\ 10^{-1}$ | $2.00\ 10^{-2}$ |
| 40 ppm | $2.04\ 10^{-2}$ | 3.50 | $8.05\ 10^{-1}$ | $6.62\ 10^{-3}$ |
| Cultive medium (Control) | $5.83\ 10^{-3}$ | | $2.30\ 10^{-1}$ | $5.80\ 10^{-3}$ |
| Manose 0.05 M (Control) | $2.85\ 10^{-2}$ | 4.35 | | $1.86\ 10^{-2}$ |

M: Mucus, S: supernatant

D-fagomine does not interfere negatively the adherence of the *Lactobacillus* to the mucus. In view of the cultive medium results, the D-fagomine benefits the adherence of *Lactobacillus* to mucus.

D-fagomine does not interfere negatively the adherence of the *Bifidobaterium* to the mucus.

The invention claimed is:

1. A method of coadjuvant treating a bacterial infection or microflora imbalance caused by an enteric, oral or respiratory bacteria in a subject by inhibiting the adherence and/or of the agglutination of enteric, oral or respiratory bacteria to epithelial cells, the method comprising administering to the subject a composition comprising a compound of formula (I) or a pharmaceutically acceptable salt thereof,

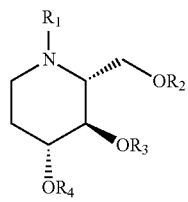

wherein $R_1$, $R_2$, $R_3$ and $R_4$ are independently selected from the group consisting of H, $(C_1-C_{11})$-alkyl, and $CH_2Ph$; in such an amount that the compound of formula (I) acts only as a coadjuvant agent; and the bacterial infection is caused by a bacteria selected from the group consisting of *Streptococcus mutants, Salmonella tphimurium, Escherichia coli Streptococcus mitis, Streptococcus oralis, Streptococcus gordanii, Porphyromonas gingivalis, Aggregatibacter actinomycetemcomitans, Fusobacterium necleatum* and *Actinomices naeslundii*, wherein administering the compound of formula (I) or a pharmaceutically acceptable salt thereof comprises administering the compound of formula (I) or a pharmaceutically acceptable salt thereof at a concentration of from 10 ppm to 40 ppm.

2. The method according to claim 1, wherein $R_1$, $R_2$, $R_3$ and $R_4$ are H.

3. The method according to claim 1, wherein the bacterial infection is caused by a bacterium selected from the group consisting of *Streptococcus mutans, Salmonella typhimurium,* and *Escherichia coli.*

4. The method according to claim 1, wherein the bacterial infection causes a disease selected from the group consisting of dental disease, periodontal disease, urinary disease and intestinal disease.

5. The method according to claim 1, wherein the composition is a food composition, a feed composition or a pet food composition.

6. The method according to claim 1, further comprising administering a saccharide, probiotics, or an antibacterial agent.

7. The method according to claim 6, comprising sequential, simultaneous, or separate administration.

8. The method according to claim 1, wherein the composition further comprises a saccharide, probiotics, or an antibacterial agent.

9. The method according to claim 8, wherein the composition is a food, pet food or feed composition.

* * * * *